(12) United States Patent
Buchberger (10) Patent No.: US 10,314,337 B2
(45) Date of Patent: Jun. 11, 2019

(54) AEROSOL-FORMING MEMBER

(71) Applicant: BATMark Limited, London (GB)

(72) Inventor: Helmut Buchberger, St. Florian (AT)

(73) Assignee: BATMark Limited, London (GB)

( * ) Notice: Subject to any disclaimer, the term of this patent is extended or adjusted under 35 U.S.C. 154(b) by 369 days.

(21) Appl. No.: 15/115,583

(22) PCT Filed: Jan. 28, 2015

(86) PCT No.: PCT/GB2015/050193
§ 371 (c)(1),
(2) Date: Jul. 29, 2016

(87) PCT Pub. No.: WO2015/114327
PCT Pub. Date: Aug. 6, 2015

(65) Prior Publication Data
US 2017/0188630 A1     Jul. 6, 2017

(30) Foreign Application Priority Data

Jan. 29, 2014   (GB) .................................. 1401519.2

(51) Int. Cl.
| | |
|---|---|
| *A61M 15/06* | (2006.01) |
| *H05B 3/34* | (2006.01) |
| *A24F 47/00* | (2006.01) |
| *A61M 11/04* | (2006.01) |

(52) U.S. Cl.
CPC ......... *A24F 47/008* (2013.01); *A61M 11/042* (2014.02); *A61M 15/06* (2013.01); *H05B 3/34* (2013.01); *A61M 2205/3368* (2013.01); *A61M 2205/3633* (2013.01); *A61M 2205/3653* (2013.01); *A61M 2205/8206* (2013.01); *H05B 2203/021* (2013.01)

(58) Field of Classification Search
None
See application file for complete search history.

(56) References Cited

U.S. PATENT DOCUMENTS

| | | | |
|---|---|---|---|
| 6,155,268 A | 12/2000 | Takeuchi | |
| 8,948,578 B2 * | 2/2015 | Buchberger | ......... A61M 11/041 392/395 |
| 2010/0200006 A1 | 8/2010 | Robinson | |

(Continued)

FOREIGN PATENT DOCUMENTS

| | | |
|---|---|---|
| CN | 201238609 Y | 5/2009 |
| EP | 2 340 729 A1 | 7/2011 |

(Continued)

OTHER PUBLICATIONS

International Search Report for corresponding International App No. PCT/GB2015/050193 dated Apr. 10, 2015; 4 pages.
Written Opinion of the International Searching Authority for corresponding International App No. PCT/GB2015/050193 dated Apr. 10, 2015; 9 pages.

(Continued)

*Primary Examiner* — Thor S Campbell
(74) *Attorney, Agent, or Firm* — Patterson Thuente Pedersen, P.A.

(57) ABSTRACT

An aerosol-forming member comprising a sheet of material configured to wick and to heat a solution. The sheet of material has a first section and a second section. The first section extends at an angle relative to the second section, wherein the first section is configured to be heated relative to the second section.

22 Claims, 10 Drawing Sheets

(56) References Cited

U.S. PATENT DOCUMENTS

| | | | |
|---|---|---|---|
| 2011/0155153 A1* | 6/2011 | Thorens | H05B 3/58 131/329 |
| 2011/0226236 A1* | 9/2011 | Buchberger | A61M 11/041 128/200.23 |
| 2011/0277756 A1 | 11/2011 | Minskoff | |
| 2013/0081623 A1* | 4/2013 | Buchberger | A61M 11/041 128/203.27 |
| 2013/0333700 A1* | 12/2013 | Buchberger | A24F 47/008 128/203.26 |
| 2014/0202454 A1* | 7/2014 | Buchberger | A24F 47/008 128/200.14 |
| 2017/0027225 A1* | 2/2017 | Buchberger | A24F 47/008 |
| 2017/0042245 A1* | 2/2017 | Buchberger | H05B 3/12 |
| 2017/0188629 A1 | 7/2017 | Dickens | |
| 2017/0188630 A1* | 7/2017 | Buchberger | A24F 47/008 |
| 2017/0238611 A1* | 8/2017 | Buchberger | A61M 15/0091 |
| 2017/0280771 A1* | 10/2017 | Courbat | A24F 47/008 |
| 2017/0318862 A1* | 11/2017 | Mironov | A24F 47/008 |

FOREIGN PATENT DOCUMENTS

| | | |
|---|---|---|
| GB | 2421436 A1 | 6/2006 |
| RU | 94815 U1 | 6/2010 |
| WO | WO2011109849 | 9/2011 |
| WO | WO 2013/057185 A1 | 4/2013 |

OTHER PUBLICATIONS

International Preliminary Report on Patentability for corresponding International App No. PCT/GB2015/050193 dated Aug. 11, 2016; 11 pages.
Chinese Office Action, Application No. 201580006116.9, dated Mar. 20, 2018, 7 pages (17 pages with translation).
Great Britain Search Report, Application No. GB1401519.2, dated Aug. 20, 2014, 6 pages.
Russian Office Action, Application No. 2016131329, dated Jan. 23, 2018, 6 pages.

* cited by examiner

AEROSOL-FORMING MEMBER

RELATED APPLICATIONS

The present application is a National Phase entry of PCT Application No. PCT/GB2015/050193, filed on 28 Jan. 2015, which claims priority to GB Patent Application No. 1401519.2, filed on 29 Jan. 2014, which are hereby fully incorporated herein by reference.

TECHNICAL FIELD

The disclosure relates to an aerosol-forming member for an aerosol delivery device. The disclosure also relates to an aerosol delivery device component comprising the aerosol-forming member according to the invention, and an aerosol delivery device comprising said aerosol delivery device component.

BACKGROUND

An aerosol delivery device is a device used for delivering substances into the body via the lungs. One type of aerosol delivery device forms a vapor of a solution in which the substances are dissolved. This vapor condenses within the aerosol delivery device as it mixes with air so as to form droplets or aerosol which is suitable for inhalation. These aerosol delivery devices may comprise a heating element that is configured to evaporate the solution held within the aerosol delivery device so as to form said aerosol. Alternatively, some aerosol delivery devices may utilize piezo atomizers to generate the aerosol.

SUMMARY

According to an aspect, there is provided an aerosol-forming member comprising a sheet of material configured to wick and to heat a solution, the sheet of material has a first section and a second section, the first section extends at an angle relative to the second section, wherein the first section is configured to be heated relative to the second section.

In one embodiment, the second section may extend about the first section so as to form a channel in which the first section is suspended.

In one embodiment, the sheet of material may further comprise a third section extending from the first section.

The first section may be configured to be heated relative to the third section.

In another embodiment, the second and third sections may extend about the first section so as to form a channel in which the first section is suspended.

In yet another embodiment, the first section may extend between the second and third sections, and the second and third sections extend at an angle relative to the first section so as to form a channel.

The sheet of material may have a U-shaped cross-section.

In one embodiment, the channel may be tubular.

In another embodiment, the first section may be planar.

In one embodiment, the sheet of material may comprise a capillary structure configured to wick a solution. The capillary structure may be exposed on both sides of the sheet of material.

In another embodiment, the sheet of material comprises a first layer capable of being heated and a second layer comprising a capillary structure.

The sheet of material may be formed with slots extending across the second and/or third sections towards the first section so as to enable the first section to be heated relative to the second and/or third sections.

In one embodiment, the sections are discrete portions joined together, the first section is made of a material that is capable of being heated relative to the material of the other section(s).

In an alternative embodiment, the sheet of material is formed from a first set of fibers, and a second set of fibers are incorporated into the first section, wherein the second set of fibers is capable of being heated relative to the first set of fibers.

According to another aspect, there is provided an aerosol delivery device component comprising an air inlet and an air outlet fluidly communicating via an aerosol chamber defined by a chamber wall, and an aerosol-forming member as described above, wherein the aerosol-forming member is at least partially located in the aerosol chamber. Alternatively, the whole aerosol-forming member may be located in the aerosol chamber.

In one embodiment, the sheet of material may comprise two opposing major surfaces that are aligned with a direction of flow of air through the aerosol chamber.

In another embodiment, at least a portion of the second section contacts the chamber wall and the first section is suspended across the aerosol chamber.

The shape of the aerosol chamber may correspond to the shape of the aerosol-forming member such that the aerosol-forming member contacts the chamber wall.

In one embodiment, the chamber wall may comprise a liquid reservoir matrix configured to replenish the aerosol-forming member with a solution.

The liquid reservoir matrix may have a capillary structure.

In one embodiment, at least the second section contacts the liquid reservoir matrix, and the capillary structure of the aerosol-forming member and the capillary structure of the liquid reservoir matrix fluidly communicate with each other.

In another embodiment, the aerosol delivery device component further comprises a heat shield locating in the aerosol chamber against the chamber wall.

According to yet another aspect, there is provided an aerosol delivery device comprising an aerosol delivery device component as described above.

BRIEF DESCRIPTION OF THE DRAWINGS

Embodiments will now be described, by way of example only, with reference to the accompanying drawings in which.

DETAILED DESCRIPTION

Figure 1:
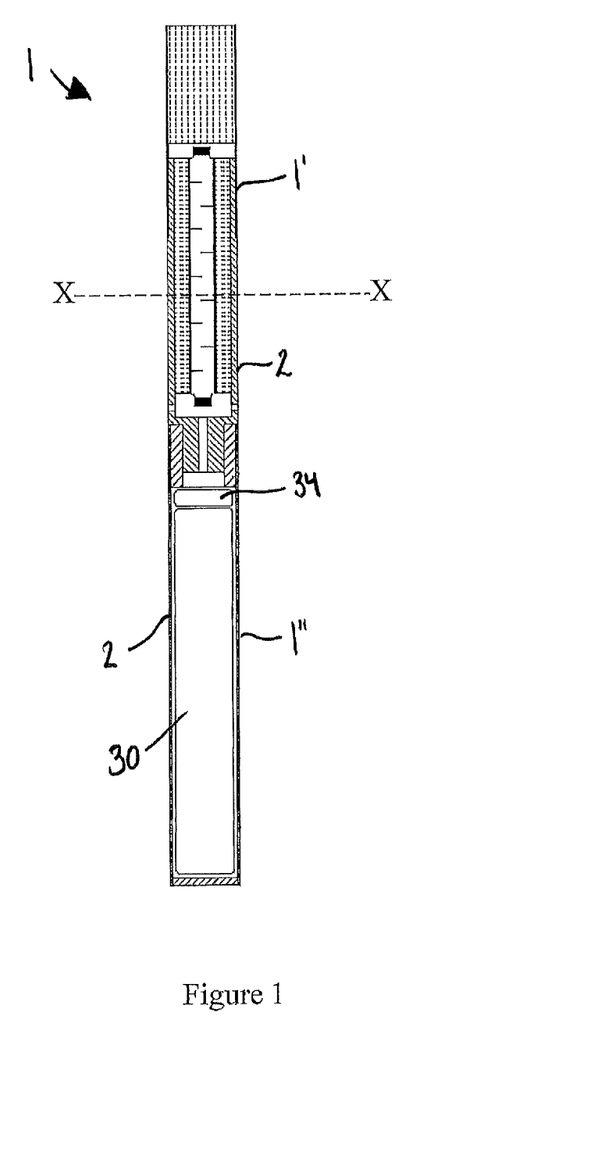
FIG. 1 shows a cross-sectional side view of an aerosol delivery device comprising an aerosol-forming member according to an embodiment.

Referring now to FIG. 1, an aerosol delivery device 1 according to an embodiment is disclosed. The aerosol delivery device comprises an aerosol delivery device component 1', and an energy store component 1". The aerosol delivery device component 1' is removably attachable to the energy store component 1", however it is envisaged that in an alternative embodiment, the aerosol delivery device component 1' and the energy store component 1" are inseparable such that they form as a single component.

The aerosol delivery device component 1' may be disposable and the energy store component 1" may be reusable. However, it is envisaged that when the two components are formed as a single component then the aerosol delivery device may be disposable or reusable.

The energy source component 1" comprises a housing holding a battery 30 and an electric circuitry 34 as shown in FIG. 1. It should be appreciated that an alternative power source to a battery may be used.

Figure 2:
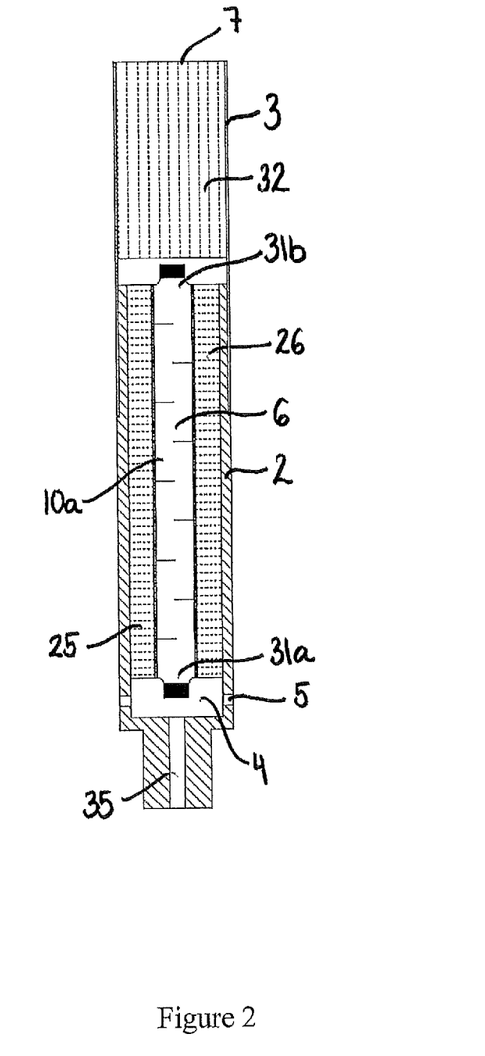
FIG. 2 shows a cross-sectional side view of an aerosol delivery device component according to the present embodiment.

The aerosol delivery device component 1' is shown in greater detail in FIG. 2 and it comprises a housing 2 formed with a mouthpiece 3 at one end and an attachment end formed with a connecting passage 35 at the opposite end. The connecting passage 35 electrically connects components held in the aerosol delivery device component 1' with the battery 30 disposed in the energy store component 1" via the electric circuitry 31.

The housing 2 is further formed with an air passage extending through the aerosol delivery device component 1'. The air passage comprises an air inlet 5, plenum chamber 4, chamber inlet 31a, aerosol chamber 6, chamber outlet 31b and outlet aperture 7. In use air is drawn in through the air inlet 5, into the plenum chamber 4, then to the chamber inlet 31a which supplies the air into the aerosol chamber 6, the air then exits the aerosol chamber 6 via the chamber outlet 31b and leaves the aerosol delivery device component 1' via the outlet aperture 7 formed in the mouthpiece 3.

Figure 3:
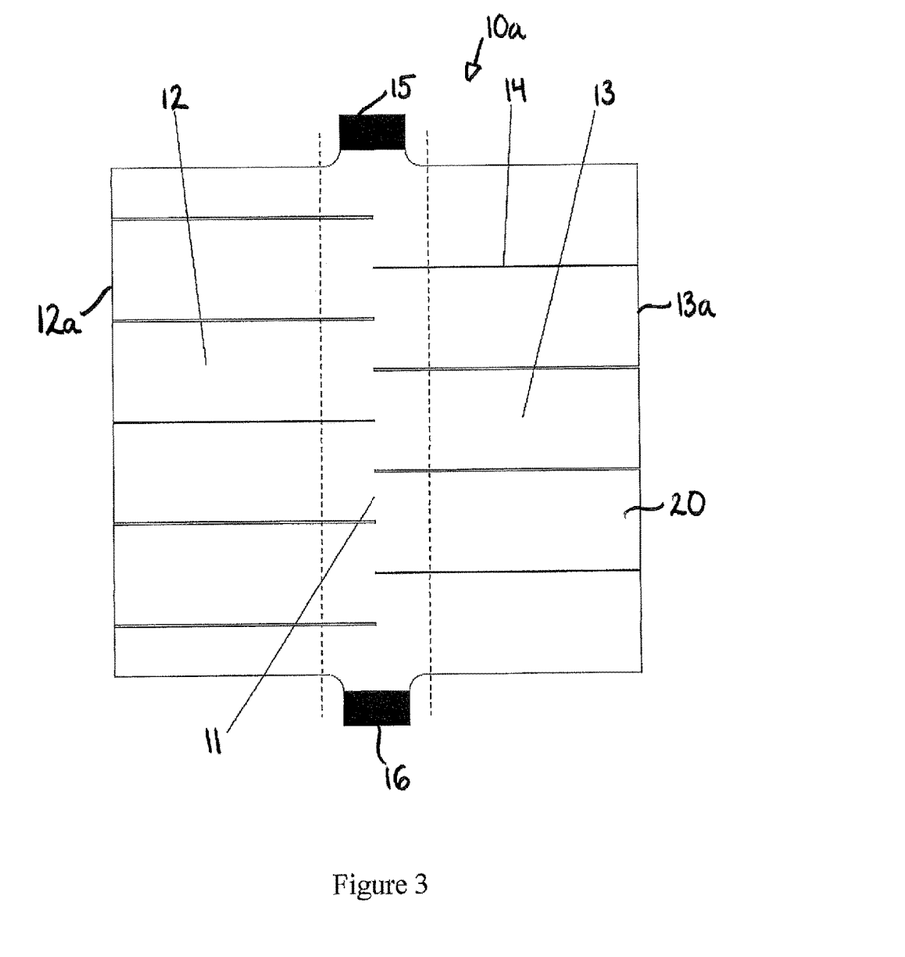
FIG. 3 shows a top planar view of an embodiment of an aerosol-forming member in an unfolded state.

An aerosol-forming member 10a is located in the aerosol chamber 6. The aerosol-forming member is shown in FIG. 3 and comprises a sheet of material that is configured to wick and heat a solution such that the sheet of material can absorb solution and thereafter heat it up such that it evaporates and forms a vapor. The sheet of material is sheet-like in nature and comprises two major opposing surfaces 20, 21. The sheet of material may comprise an open-pored structure, foam structure or interconnecting network of pores, all of which form a capillary structure. The capillary structure enables the aerosol-forming member 10a to wick or absorb a solution. The term "capillary structure" used herein is to be understood as a structure through which liquid or a solution can travel as a result of capillary action.

The aerosol-forming member 10a may be made of a porous, granular, fibrous or flocculent sintered metal(s) so as to form a capillary structure. In another embodiment, the aerosol-forming member 10a comprises an open-pored metallic foam or a group of layers of wire mesh or calendered wire mesh which also form capillary structures. The aerosol-forming member 10a may be formed from stainless steel. Furthermore, the aerosol forming member 10a may be formed with a capillary structure that extends throughout the whole aerosol-forming member 10a such that it is exposed on the two major surfaces 20, 21 of the sheet of material. In an embodiment, one of the major surfaces 20, 21 may be sealed with a metallic foil or cover that is sintered or attached to said major surface. Alternatively, a region of one or both of the major surfaces 20, 21 may be sealed. In another embodiment, the aerosol-forming member 10a is configured such that the capillary structure does not extend throughout the whole aerosol-forming member. In yet another un-illustrated embodiment, a thin support layer may be sintered onto one or both of the major surfaces 20, 21. Such a support layer may be formed from a wire mesh made of stainless steel.

The material from which the aerosol-forming member 10a is formed is heatable in that it comprises sufficient electrical resistivity so that when current is passed through, the aerosol-forming member 10a heats up to a temperature sufficient to cause the solution held in the capillary structure to evaporate or vaporize. In these embodiments, the aerosol-forming member 10a can be considered to comprise a heating element formed with a capillary structure such that the heating element and the capillary structure are integrated and form a single entity or unit.

In the above described embodiments wherein the sheet of material comprises a single layer configured to wick and heat a solution, the sheet of material can be described as comprising a heating element and a wick that are arranged in the same surface.

Alternatively the aerosol-forming member 10a may comprise any combination of the aforementioned structures and materials, e.g. by providing multiple layers of different structures/materials, the layers being joined together, e.g. by sintering. One such alternative un-illustrated embodiment will now be described in more detail.

The aerosol-forming member comprises a sheet of material that is sheet-like in nature and formed from a plurality of layers. For example, the aerosol-forming member 10a may comprise a first heatable layer acting as a heating element. This first layer is formed from a material that is configured to be heated up. The aerosol-forming member 10a may further comprise a second layer formed with an open-pored structure, foam structure or interconnecting network of pores, all of which form a capillary structure. The capillary structure enables the aerosol-forming member 10a to wick or absorb a solution. This second layer may be made of a porous, granular, fibrous or flocculent sintered metal(s) so as to form the capillary structure. Alternatively, the second layer may comprise an open-pored metallic foam or a group of layers of wire mesh or calendered wire mesh forming the capillary structure. The second layer may be made of stainless steel. This second layer acts as a wick.

The first layer (heating element) and the second layer (wick formed with a capillary structure) are laid on top of each other so as to form a sheet of material having two opposing major surfaces, wherein the capillary structure is exposed on one of the major surfaces. In this embodiment, the sheet of material can be described as comprising a heating element and a wick arranged in parallel surfaces.

In an alternative un-illustrated embodiment, the first layer also comprises a capillary structure as described above with reference to the second layer, such that the first layer can both heat and wick a solution. In this embodiment, the sheet of material can be described as comprising a heating element and a wick that are arranged in the same surface and in parallel surfaces.

In an alternative un-illustrated embodiment, the sheet of material comprises a third layer that is similar to the second layer in that it comprises a capillary structure. The second and the third layer sandwich the first layer such that the capillary structure is exposed on both major surfaces of the sheet of material.

The sheet of material according to any of the above described embodiments has a thickness or depth that falls within the range of 20-500 μm. Alternatively, the thickness falls within the range of 50 to 200 μm. The thickness or depth should be understood as meaning the distance between the two major surfaces 20, 21 of the sheet of material.

Figure 4:
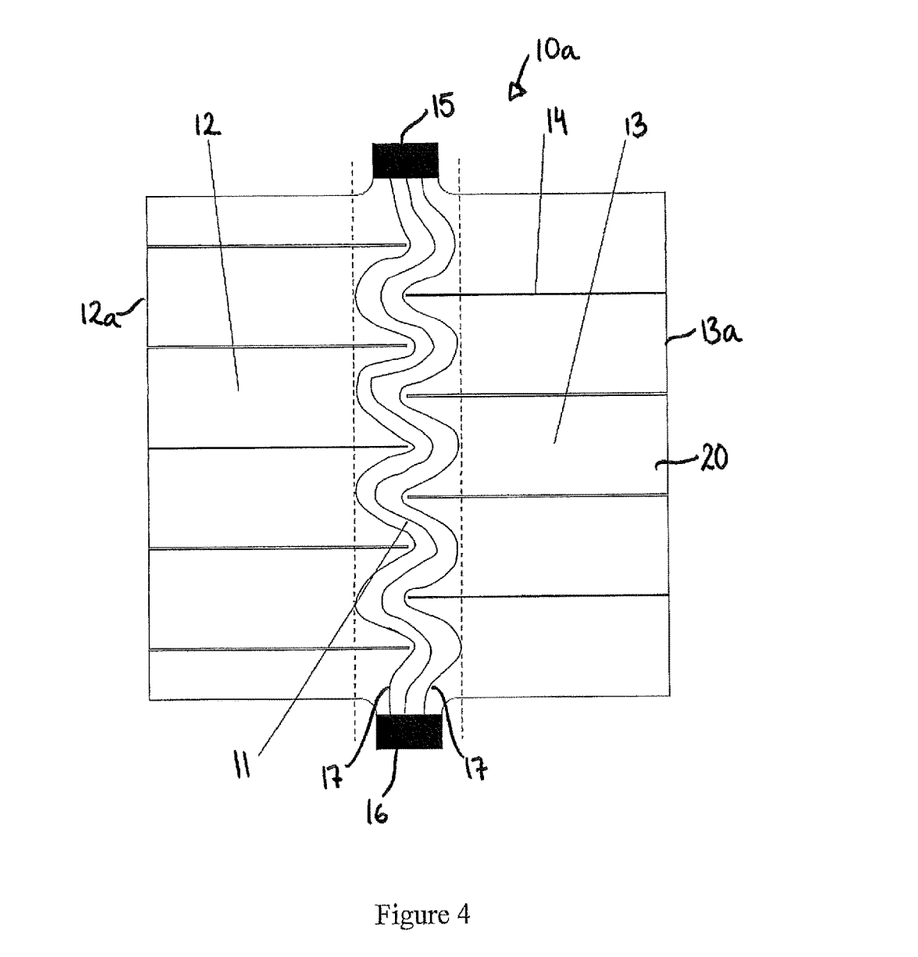
FIG. 4 shows a top planar view of an electrical field of the aerosol-forming member in FIG. 3.
Figure 5:
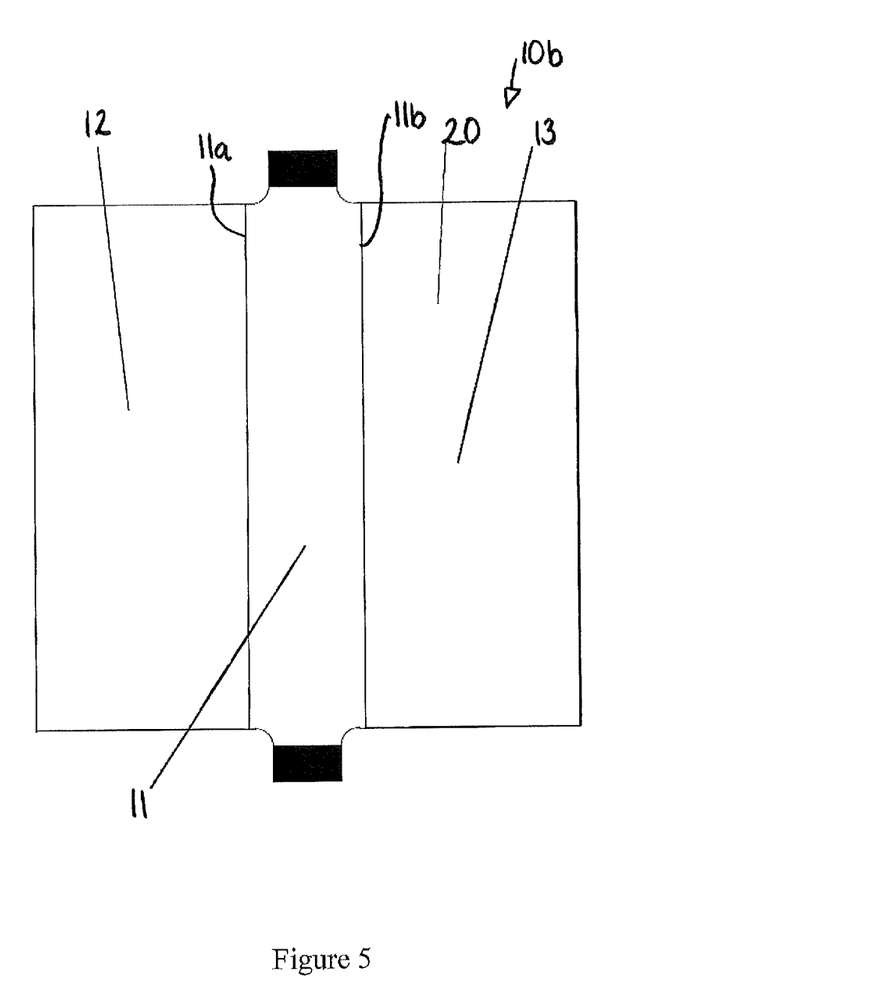
FIG. 5 shows a top planar view of another embodiment of an aerosol-forming member in an unfolded state.
Figure 6:
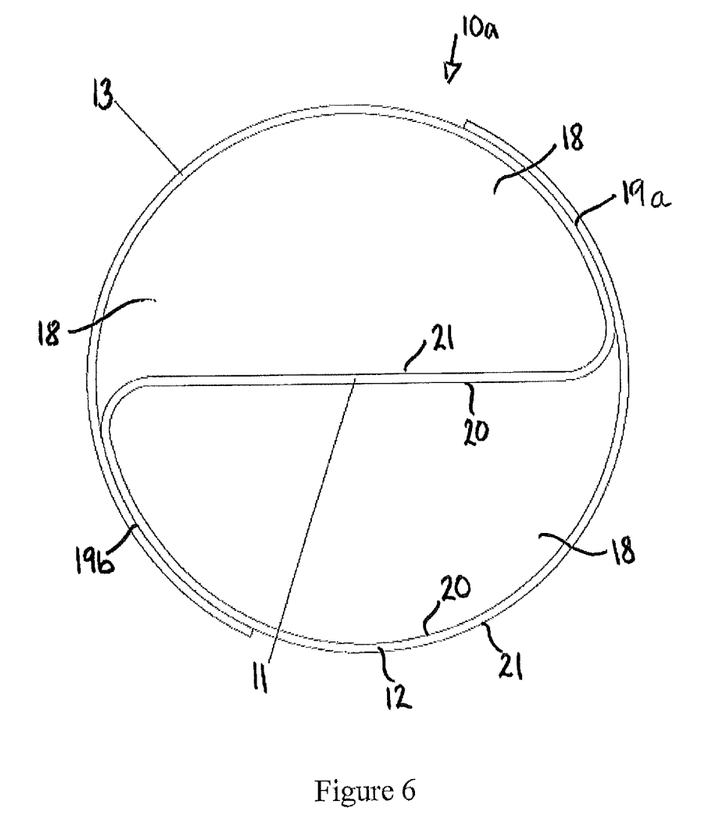
FIG. 6 shows a cross-sectional view of an embodiment of an aerosol-forming member in a folded state.

FIGS. 3 and 4 show the aerosol-forming member 10a in an unfolded state or position and FIG. 6 shows the aerosol-forming member 10a in a folded state or position. The sheet of material has a first or central section 11 and a second and a third section 12, 13 on either side of the central section 11. The dashed lines in FIG. 3 represent the boundaries between the sections 11, 12, 13. The second 12 and third 13 sections are formed with slots or notches 14 that extend from opposing long edges 12*a*, 13*a* of the aerosol-forming member 10*a* towards and into the first section 11. In the embodiment shown in FIG. 3, the second section 12 is formed with five slots 14 and the third section 13 is formed with four slots 14. The slots 14 are parallel to one another and spaced apart across the second and third sections 12, 13.

Opposing free ends of the first section 11 act as electrical terminals 15, 16. The electrical terminals 15, 16 are configured to be electrically connected, e.g. via an electric circuitry 34, to a power source, such as the battery 30, so that an electric current can be passed across the aerosol-forming member 10*a*. The electrical terminals 15, 16 may extend from the first section as seen in FIG. 2 enabling them to slot into connection holes (not shown) of the aerosol delivery device, the connection holes being electrically connected to the power source. Alternatively, an electrically conductive wire connected to the power source may be clipped or soldered onto each electrical terminals 15, 16 so that a current can be passed across the aerosol-forming member 10*a*. In an alternative un-illustrated embodiment the electrical terminals are in line with adjacent edges of the second and third sections 12, 13 such that the terminals do not protrude. These terminals may be connected to an electrically conductive wire via a clip and/or the wire may be soldered onto the terminals. It should also be understood that the electrical terminals may be of any other shape and it is envisaged that other means suitable for connecting the electrical terminals to the power source may be used.

When a current is passed through the aerosol-forming member 10*a*, the slots 14 compress the electric field 17 such that it is substantially contained within the first section 11 as illustrated in FIG. 4. The dashed lines in FIG. 4 represent boundaries between the first, second and third sections 11, 12, 13. As a result, the first section 11 is primarily or directly heated up whilst the second and third sections 12, 13 remain relatively unheated, however it should be appreciated that the heat emitted from the first section 11 might cause the second and third sections 12, 13 to heat up slightly.

It is envisaged that the present invention is not limited to an aerosol-forming member 10*a* comprising slots so as to contain the heat within the first section 11. In an alternative embodiment as shown in FIG. 5, the sheet of material comprises a single layer made up of discrete sections that are chemically and/or mechanically connected to one another. In other words, the first section 11 is chemically and/or mechanically connected to the second and third sections 12, 13. The first section 11 is made of a material of high electrical resistivity whereas the second or the third sections 12, 13 are formed from a material with low electrical resistivity such that when a current is passed through the first section, the electrical field is substantially contained within the first section. It should be understood that the first section may also be formed with a capillary structure such that it extends throughout the whole aerosol-forming member. The difference in electrical resistivity results in that the first section 11 heats up relatively to the second and third sections 12, 13.

In a specific embodiment the first section 11 comprises a conductive material such as stainless steel wire mesh, the second and third sections 12, 13 comprise a fiber web or fabric made of glass fibers, glass fiber yarns or any other non-conductive and inert fiber materials. The fiber web or fabric of the second and third sections 12, 13 may be joined with the wire mesh of the first section 11 by fritting, that is to say by partially melting the glass phase in the contact zone.

In an alternative un-illustrated embodiment, the aerosol forming member comprises a sheet of material comprising a plurality of layers similar to the un-illustrated embodiment described above. However, in this embodiment, the sheet of material comprises discrete sections, a first, second and a third section, such that each section has a plurality of layers. The first section is chemically and/or mechanically connected to the second and the third section. At least one layer of the first section is made of a material of high electrical resistivity whereas the layers of the second or the third sections are formed from a material with low electrical resistivity such that when a current is passed through the first section, the electrical field is substantially contained within the first section. As a result, the first section heats up relatively to the second and third sections.

In yet another alternative un-illustrated embodiment, the sheet of material does not comprise discrete portions or slots so that the first section is heated up relative to the second and third sections 12, 13. An example of such an embodiment is wherein the sheet of material comprises a non-conductive fiber web or fabric made of glass fibers, glass fiber yarns or any other non-conductive and inert fiber materials. The fiber web or fabric is providing the capillary structure and extends throughout all sections of the sheet of material. Conductive fibers or wires are incorporated in the fiber web or fabric in a first or central section of the sheet of material making said first or central section heatable. The conductive fibers or wires may be made of stainless steel or of a heating wire alloy like Chromium Nickel. Alternatively, conductive fibers may replace non-conductive fibers and conductive wires (heating wires) may replace non-conductive yarns.

It should be understood that alternative configurations of the aerosol-forming member wherein the heat is contained within the first section relative to the second and third sections are intended to fall within the scope of the disclosure.

FIG. 6 shows the aerosol-forming member 10*a* in a folded state or position. The second and third sections 12, 13 are folded about the first section 11 such that the second and third sections 12, 13 enclose the first section 11 and form a channel 18. The second and third sections 12, 13 are folded about the first section 11 such that they form a tube or tubular channel. Regions 19*a*, 19*b* of the second and third sections 12, 13 overlap such that the channel 18 is completely enclosed in a direction about the first section 11. The first section 11 is planar or flat and suspended in the channel 18 such that it extends across the channel 18.

It should be understood that the second and third sections 12, 13 do not have to form a tubular channel 18. In alternative un-illustrated embodiments the second and third sections 12, 13 are folded about the first section 11 such that they form a channel having an oval, square, rectangular or any other type of polygonal cross-section.

It should also be appreciated that the first section 11 is not limited to being planar or flat. In an alternative un-illustrated embodiment, the first section 11 comprises corrugations having ridges and grooves such that it follows a meandering or oscillating path, or a sinusoidal curve. The ridges and grooves may extend in a direction parallel to the opposing long edges 12*a*, 13*a* of the sheet of material.

Figure 7:
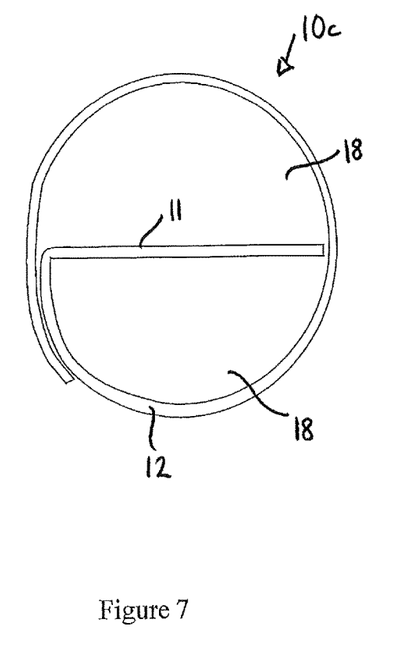
FIG. 7 shows a cross-sectional view of an aerosol-forming member in a folded state according to another embodiment.

In yet another embodiment as shown in FIG. 7, the third section 13 is omitted such that the aerosol-forming member 10*c* comprises a first and a second section 11, 12 only. The second section 12 extends from the first section 11 and folds about the first section 11 such that the second section 12 forms a channel 18 and the first section 11 is suspended across the channel 18. Alternatively, the second section 12 partially encloses the first section 11. For example, the second section 12 may extend around a single surface of the first section such that the cross-section of the aerosol-forming member has a semi-circular shape.

Figure 8:
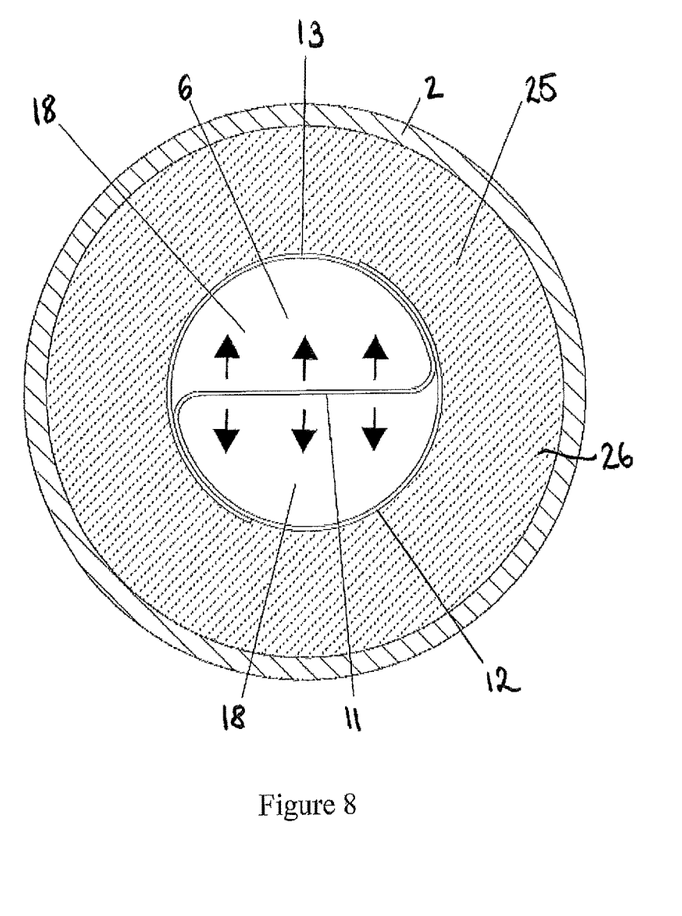
FIG. 8 shows a cross-sectional view of the aerosol delivery device along the line X-X of FIG. 1.

Referring now to FIG. 8, the aerosol-forming member 10*a* is located in the aerosol chamber 6 defined by a chamber wall 25 formed from a liquid reservoir matrix. The liquid reservoir matrix 26 comprises a capillary structure, for example an interconnecting porous or open-porous structure, such that it can hold a solution or liquid. The liquid reservoir matrix 26 may be formed from a fiber material, for example polyethylene or polyester fibers.

The shape of the aerosol chamber 6 defined by the chamber wall 25 corresponds to the shape of the aerosol-forming member 10*a* such that when the aerosol-forming member 10*a* is received in the aerosol chamber 6 it contacts the chamber wall 25. In the embodiment shown in FIG. 8, the second and third sections 12, 13 contact the chamber wall 25, however it should be understood that only one of the second and third sections 12, 13 may contact the chamber wall 25. Alternatively, if the aerosol-forming member only comprises a second section 12 as seen in FIG. 7 then only the second section is in contact with the chamber wall 25. It should also be understood that it is not necessary for the whole second and/or third sections 12, 13 to contact the chamber wall 25. For example, only a portion of the second and/or third sections may contact the chamber wall 25.

In the embodiments of the present disclosure, the first section 11 is suspended across the aerosol chamber 6 which can be appreciated form FIG. 8.

Advantageously, the liquid reservoir matrix 26 does not have to be made out of a heat resistant material as it is shielded from the heat of the first section 11 by the second and/or third sections 12, 13 that are not substantially heated up during operation of the aerosol delivery device 1.

The liquid reservoir matrix 26 holds a solution that is formed into aerosol by the aerosol-forming member 10*a*. The solution is drawn or absorbed into the aerosol-forming member 10*a* by capillary action via the capillary structure of the second and the third sections 12, 13. The solution is spread throughout the whole capillary structure of the aerosol-forming member 10*a*, i.e. the first, second and third sections 11, 12,13. When the first section 11 is heated up, the solution evaporates from the first section 11 so as to form a vapor which upon condensation forms an inhalable aerosol. Thereafter, and even during the heating, the first section 11 is replenished with solution by capillary action moving solution from the liquid reservoir matrix 26, via the second and third sections 12, 13 to the first section 11. This is described in more detail below.

The capillarity of the aerosol-forming member 10*a* may be greater than the capillarity of the liquid reservoir matrix 26 so as to induce flow of solution from the liquid reservoir matrix 26 towards the aerosol-forming member 10*a*. The capillarity is defined by the pore size and the wetting conditions of the respective capillary structures.

As previously described, the power source enabling the aerosol-forming member 10*a* to heat up may be a battery 30. The battery 30 is controlled by a controller (not shown) and the electric circuitry 34 which may be mounted on a printed circuit board (PCB). The electrical terminals 15, 16 of the aerosol-forming member 10*a* are electrically connected to the positive and negative terminals of the battery 30 respectively as previously described. When current is drawn from the battery 30 and through the sheet of material, the electrical resistance of the sheet of material causes the first section 11 of the sheet of material to increase in temperature. In the embodiment wherein the sheet of material comprises several layers, the resistance of the conductive layer acting as a heating element causes the first section 11 to increase in temperature, which in turn heats up the adjacent non-conductive second and/or third layers of the first section 11. The current drawn by the battery 30, and thus the temperature of the sheet of material may be controlled by a switching circuit, e.g. a Power-MOSFET switching circuit, which is provided on the PCB disposed within the housing 2. The switching circuit may provide automatic control of the temperature, for example, by using temperature sensors (not shown), or may be controlled by a button or dial (now shown) provided on the housing 2 that may be manipulated by the user.

Operation of the aerosol delivery device 1 will now be described with reference to FIGS. 1 and 8. In use, the user may manually activate the aerosol delivery device 1 or the aerosol delivery device 1 may be activated automatically as the user starts puffing on the aerosol delivery device 1. This may be achieved by a pressure sensor (not shown) mounted on the PCB and communicating with the plenum chamber 4 via the connecting passage 35. In either embodiment, the battery 30 provides a potential difference between the electrical terminals 15, 16 of the aerosol-forming member 10*a* as the aerosol delivery device is activated, causing current to flow between the electrical terminals 15, 16 such that the first section 11 of the sheet of material increases in temperature. The heat is contained within the first section 11 due to the slots 14, however it should be appreciated that the heat may be contained within the first section by other means as described above. This increase in temperature causes the solution held in the capillary structure of the first section 11 of the sheet of material to evaporate so as to form a vapor. The vapor mixes with air drawn into the aerosol delivery device 1 via plenum chamber 4 and chamber inlet 31*a* by the user. The vapor mixes with air in the aerosol chamber 6, and as this occurs the vapor condenses and forms droplets such that an inhalable aerosol is produced.

The aerosol-forming member 10*a* according to any of the above described embodiments is located in the housing such that the planes of the major surfaces 20, 21 are parallel to or substantially aligned with the direction of the airflow through the aerosol chamber 6. Thus, when a solution is held in the aerosol-forming member 10*a* and it is heated up such that the solution evaporates, the solution evaporates in a direction transverse to the direction of the airflow. In the embodiments wherein the capillary structure is exposed on both sides of the sheet of material, the solution is evaporated from both sides in opposite directions as indicated by the arrows in FIG. 8. The vapor mixes with air so as to form aerosol in the channel 18 formed by the second and/or third sections 12, 13. The channel 18 directs the flow of aerosol through the aerosol delivery device towards the user. Furthermore, as a result of the channel 18, solution is evaporated from the major surfaces 20, 21 of the first section 11 in a direction towards the major surfaces 20, 21 of the second and third sections 12, 13. This results in reduced levels of vapor condensing on the chamber wall and other internal components as the major surfaces 20, 21 of the second and third sections 12, 13 are shielding the chamber wall and said other internal components. Furthermore, as the aerosol-forming member 10*a* cools down aerosol remaining in the aerosol chamber 6 that condenses onto one of the major surfaces 20, 21 will also be reabsorbed into their capillary structure and re-evaporated as the aerosol-forming member 10*a* is reactivated and heats up again.

The configuration of the aerosol-forming member 10*a* forming a channel 18 reduces condensation from forming on the chamber wall, internal components and/or inner walls of the housing 2. Thus, sponges or other means for absorbing condensation not inhaled by the user that are used in some conventional aerosol delivery devices may be omitted. This results in a more compact aerosol delivery device 1, as well as a simplified manufacturing process and reduced costs. Furthermore, by reducing the amount of aerosol and/or vapor from condensing onto inner walls of the housing 2, the transfer of condensation heat to the housing 2 may be reduced, making the aerosol delivery device 1 more comfortable for the user to hold.

After the aerosol-forming member 10*a* has been activated and aerosol has formed in the channel 18, the aerosol is drawn through the channel 18 as the user continues to inhale. The aerosol then exits the aerosol chamber 6 through a chamber outlet as seen in FIG. 2. The aerosol then passes through an optional aerosol refining member 32 provided in the housing 2, causing the aerosol to be cooled. The refining member 32 may also contain flavoring agents like menthol that are released into the flow of aerosol before entering the user's mouth via the outlet aperture 7 provided in the mouthpiece 3. Meanwhile, the solution that has evaporated from the capillary structure of the first section 11 of the sheet of material is replaced by fresh solution from the liquid reservoir matrix 26 due to the capillary effect of the capillary structure as described above and the second and/or third section being in contact with the liquid reservoir matrix 26. Fresh air enters the channel 18 via the inlet aperture 5, plenum chamber 4 and chamber inlet 31*a*. In one embodiment, a pressure drop element or flow resistor 33 is positioned in the plenum chamber 4 so that the flow of air into the aerosol chamber 6 can be controlled. The flow resistor 33 may consist of a simple aperture or hole and may be identical with the inlet aperture 5 in the housing 2. Alternatively the flow resistor may consist of a porous body similar to a cigarette filter providing the flow resistance of a conventional cigarette.

Figure 9:
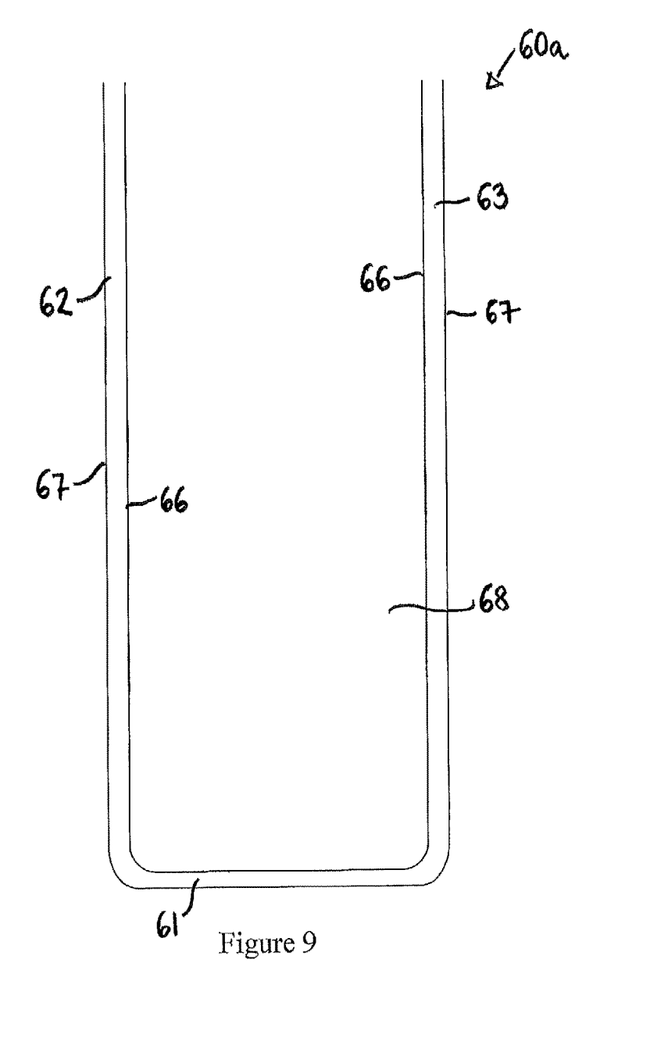
FIG. 9 shows a cross-sectional view of an aerosol-forming member according to yet another embodiment.

Referring now to FIG. 9, another embodiment of an aerosol-forming member 60*a* is shown. The aerosol-forming member 60*a* comprises a sheet of material having a first section 61 extending between a second and a third section 62, 63. The first section 61 is at a right angle relative to the second and third sections 62, 63, and the second and third sections 62, 63 are facing one another. Thus, the sheet of material has a U-shaped cross-section which defines a channel 68.

It should be understood that sheet of material is not limited to having a U-shaped cross-section. Thus, the second and third sections 62, 63 are not limited to extending at a right angle from the first section 61. The second and third sections 62, 63 may extend at an oblique angle relative to the first section 61. The second and third sections 62, 63 may extend towards one another or diverge away from one another.

The aerosol-forming member 60*a* is similar to the embodiments of the aerosol-forming member 10*a* described above with reference to FIGS. 1 and 8 and so a detailed description will be omitted. However, it should be understood that the sheet of material has two opposing major surfaces 66, 67 and that the sheet of material may be formed with slots (not shown) such that when an electric current is passed through the sheet of material the first section 61 is heated up relative to the second and third sections 62, 63. Alternatively, the first section 61 may be configured to heat up relative to the second and third sections 62, 63 according to any of the embodiments described above with reference to FIGS. 1 to 8. Furthermore, it should be understood that the aerosol-forming member 60*a* has an open-pored structure, foam structure or interconnecting network of pores, all of which form a capillary structure. The capillary structure enables the aerosol-forming member 60*a* to wick or absorb a solution. The sheet of material may comprise a single or a plurality of layers according to the various embodiments described with reference to FIGS. 1 to 8.

It is also envisaged that in an alternative un-illustrated embodiment the third section 63 is omitted such that the sheet of material comprises a first 61 and a second section 62 only extending at an angle relative to one another, for example, the aerosol-forming member may have an L-shaped cross section. In this embodiment, the first section is configured to be heated up relative to the second section by the use of slots or different materials as described above, or any other means configured to contain the heat to the first section.

Figure 10:
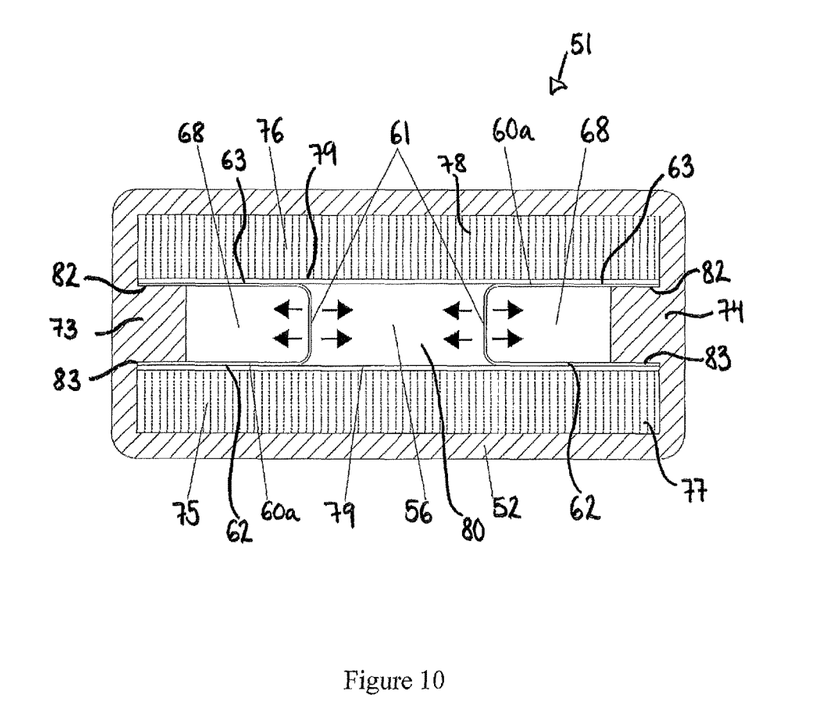
FIG. 10 shows a cross-sectional view of a further embodiment of an aerosol delivery device comprising the aerosol-forming member shown in FIG. 9.

Referring now to FIG. 10 which shows a cross-section of an aerosol delivery device 51 similar to the one shown in FIG. 1, however the aerosol delivery device 51 comprises two aerosol-forming members 60*a* as described with reference to FIG. 9.

The aerosol delivery device 51 is similar to that described with reference to FIGS. 1 and 2, and so a detailed description will be omitted. However, it should be appreciated that the aerosol delivery device comprises a housing 52 with a mouthpiece (not shown), and a passage extending therethrough. The passage comprises an inlet aperture, plenum chamber, chamber inlet, aerosol chamber 56, chamber outlet and an outlet aperture.

Two of the aerosol-forming members 60*a* described with reference to FIG. 9 are located in the aerosol chamber 56. The aerosol chamber 56 is defined by a chamber wall comprising two opposing chamber side walls 73, 74 and two opposing chamber main walls 75, 76. Each chamber main wall 75, 76 comprises a liquid reservoir matrix 77, 78. The liquid reservoir matrices 77, 78 comprise a capillary structure, for example an interconnecting porous or open-porous structure, such that it can hold a solution or liquid. The liquid reservoir matrices 77, 78 may be formed from a fiber material, for example polyethylene fibers.

The capillarity of the aerosol-forming member 60*a* may be greater than the capillarity of the reservoir matrices 77, 78 so as to induce a flow of solution from the liquid reservoir matrices 77,78 towards the aerosol-forming member 60*a*. The capillarity is defined by the pore size and the wetting conditions of the respective capillary structures.

A heat shield 79 is located along each of the liquid reservoir matrices 77, 78 such that the heat shields 79 face the aerosol chamber 56. The heat shields 79 protect the liquid reservoir matrices 77, 78 from overheating as the temperature of the aerosol-forming member 60a is increased. Furthermore, the heat shields 79 protect individual reservoir matrix fibers from extending towards the heated section 61. The heat shields 79 are porous so as to enable a capillary effect across the liquid reservoir matrices 77, 78 to the aerosol-forming member 60a. The heat shields 79 may be formed from a thin non-conductive material like oxidized stainless steel wire mesh or inert fabrics like glass or carbon fabrics. It should be understood that the heat shields 79 are optional.

It should also be understood that the present invention is not limited to comprising two liquid reservoir matrices 77, 78. It may comprise more than two liquid reservoir matrices. For example, it may comprise several discrete portions of liquid reservoir matrices. The discrete portions may feature different capillarities so as to optimize the flow of solution to the aerosol-forming member 60a. In alternative embodiment, only one chamber main wall 75, 76 comprises a liquid reservoir matrix and the other chamber main wall may be made of a non-porous material.

Each sheet of material is located in the aerosol chamber 56 such that their second and third sections 62, 63 are parallel or aligned to one another, as well as in contact with the liquid reservoir matrices 77, 78 of the chamber main walls 75, 76. However, it should be understood that only the second or the third sections 62, 63 or a portion of the second and/or third section 62, 63 of each sheet of material may be in contact with the chamber main walls 75, 76. If the aerosol chamber 56 is provided with heat shields 79, the second and third sections 62, 63 are parallel or aligned, as well as in contact with said heat shields 79. Similarly, only the second or the third sections 62, 63 or a portion of the second and/or third section 62, 63 of each sheet of material may be in contact with the heat shields 79.

The sheets of material are positioned in the aerosol chamber 56 such that each first section 61 is suspended across the aerosol chamber 56, or more specifically, suspended between the chamber main walls 75, 76. The first sections 61 of each sheet of material are parallel to one another, however this is optional.

The positioning of the sheets of material causes the first sections 61 together with the chamber main walls 75, 76 to define a central channel 80.

Ends 82, 83 of each sheet of material are sandwiched between the housing 52 and the heat shields 79 as seen in FIG. 10. This enables each sheet of material to be held in place. In the embodiment wherein the aerosol chamber 56 is not provided with heat shields 79, the ends 82, 83 of the sheets of material are sandwiched between the housing 52 and the chamber main walls 75, 76.

The aerosol-delivery device 51 further comprises a battery (not shown) and an electric circuitry that can be mounted on a printed circuit board (PCB) (not shown) as described with reference to FIGS. 1 and 8, and the aerosol-delivery device 51 is configured similar to the aerosol delivery device 1 described with reference to FIGS. 1 and 8 such that the ends 82, 83 of the aerosol-forming member 60a as seen in FIG. 10, are electrically connected to the positive and negative terminals of the battery respectively. When current is drawn from the battery and through the sheet of material of each aerosol-forming member 60a, the resistance causes the first section 61 of each sheet of material to increase in temperature relative to their second and the third sections 62, 63.

It is envisaged that the aerosol delivery device 51 may comprise a single aerosol-forming member 60a, or two or more aerosol-forming members 60a.

Operation of the aerosol delivery device 51 will now be described with reference to FIGS. 8 and 9. Similar to the aerosol-delivery device 1 described with reference to FIGS. 1 to 6, the user may manually activate the aerosol delivery device 51 or the aerosol delivery device 51 may be activated automatically as the user starts puffing on the aerosol delivery device 1. This may be achieved by a pressure sensor (not shown) mounted on the PCT and communicating with the plenum chamber 4 extending between the inlet aperture and aerosol chamber 56. In either embodiment, the battery provides a potential difference between the ends 82, 83 or electrical terminals of each sheet of material of the aerosol-forming member 60a as the aerosol delivery device 51 is activated, causing current to flow between the ends 82, 83 of each sheet of material. This causes the first section 61 of each sheet of material to increase in temperature. This increase in temperature causes the solution held in the capillary structure of the first section 61 of each sheet of material to evaporate so as to form a vapor. The vapor mixes with air drawn into the aerosol delivery device 51 by the user. The vapor mixes with air in the aerosol chamber 56, and as this occurs the vapor condenses and forms droplets such that an inhalable aerosol is produced.

The aerosol-forming members are located in the housing such that the planes of the major surfaces 66, 67 are parallel to the direction of the airflow. Thus, when a solution is held in each aerosol-forming member 60a and they are heated up such that the solution evaporates, the solution evaporates in a direction transverse to the direction of the airflow. In the embodiments wherein the capillary structure is exposed on both sides of the sheet of material, the solution is evaporated from both sides in opposite directions as indicated by the arrows in FIG. 10. Vapor is generated in the channels 68 of each sheet of material as well as the central channel 80. The vapor mixes with air flowing through the channels 68, 80 such that aerosol is formed. Furthermore, the channels 68, 80 direct the flow of aerosol through the aerosol delivery device 51 towards the user. Furthermore, as a result of the channels 68, solution is evaporated from the major surfaces 67 of the first sections 61 in a direction towards the major surfaces 67 of the second and third sections 62, 63. This results in reduced levels of vapor condensing on the chamber wall and other internal components as the major surfaces 67 of the second and third sections 62, 63 are at least partially shielding the chamber wall and said other internal components. Any condensate built up on the major surfaces 67 of the second and third sections 62,63 will be reabsorbed into the capillary structure of the aerosol-forming member 60a and evaporated as the aerosol-forming member 60a heats up again. Furthermore, as the aerosol-forming member 60a cools down aerosol remaining in the aerosol chamber 56 may condense onto the major surfaces 66, 67 of each sheet of material such that it is also reabsorbed into the capillary structure of the aerosol-forming members 60a and re-evaporated as the aerosol-forming members 60a are reactivated and heat up again. Condensate resulting from vapor/aerosol formed in the channel 80 and settling down on the inner surfaces of the chamber main walls 75, 76 will be reabsorbed into the capillary structure of the reservoir matrices 77, 78 and that way resupplied to the aerosol-forming member 60a.

Similar to the aerosol-forming member 10a described with reference to FIGS. 1 to 6, the channels 68, 80 of the aerosol-forming member shown in FIGS. 8 and 9 also reduce condensation from forming on the chamber walls, internal components and/or inner walls of the housing 52 as they direct the aerosol through part of the aerosol delivery device 51. Thus, sponges or other means for absorbing condensed aerosol not inhaled by the user that are used in some conventional aerosol delivery devices may be omitted. This results in a more compact aerosol delivery device 51, as well as simplified manufacturing processes and reduced costs. Furthermore, by reducing the amount of aerosol and/or vapor from condensing onto the inner walls of the housing 52, the transfer of condensation heat to the housing 52 may be reduced, making the aerosol delivery device 51 more comfortable for the user to hold.

After the aerosol-forming member 60*a* has been activated and aerosol has formed in the channels 68, 80, the aerosol is drawn through the channels 68, 80 as the user continues to inhale. The aerosol then exits the aerosol chamber 56 through a chamber outlet. The aerosol then passes through an optional aerosol refining member (not shown) provided in the housing 52, causing the aerosol to be cooled. The refining member may also contain flavoring agents like menthol that are released into the flow of aerosol before entering the user's mouth via the outlet aperture provided in the mouthpiece. Meanwhile, the solution that has evaporated from the capillary structure of the sheets of material is replaced by solution from the liquid reservoir matrices 77, 78 due to the capillary effect of the capillary structure and the second and third sections being in contact with the liquid reservoir matrices 77, 78. Fresh air enters the channels 68, 80 via the inlet aperture, plenum chamber and chamber inlet. In one embodiment a pressure drop element or a flow resistor (not shown) is positioned in the plenum chamber so that the flow of air into the aerosol chamber 56 can be controlled. The flow resistor may consist of a simple aperture or hole and may be identical with the inlet aperture in the housing 52. Alternatively the flow resistor may consist of a porous body similar to a cigarette filter providing the flow resistance of a conventional cigarette In any of the embodiments described herein the aerosol forming member 10*a*, 10*b*, 10*c*, 60*a* comprises a sheet of material that has a first section and a second section wherein the first section extends at an angle relative to the second section so as to form a channel. Furthermore, the first section is configured to be heated relative to the second section, and in the embodiments where the aerosol-forming member also comprises a third section, the first section is also configured to be heated relative to the third section. The first section being heated relative to the second and third sections is to be understood as the first section being heated to a sufficient temperature so as to evaporate the solution used, whereas although the second and third sections may be heated, they are not heated up to a temperature that is sufficient to evaporate the solution used. For example, if a solution has a boiling point of 100° Celsius the first section is configured to be heated up to 100° C. and above, whereas the second and third sections are configured so as to not be heated up to 100° C. and above. The second and third sections may be configured such that they are not heated above a particular temperature that might affect the function of the chamber wall.

It should be understood that the aerosol-forming member and/or liquid matrix reservoir according to the present disclosure is not limited to being used with the aerosol delivery device described and shown herein. The aerosol-forming member and/or liquid matrix reservoir according to the present disclosure can be used in any appropriate aerosol delivery device.

The above described embodiments of the aerosol-forming member 10*a*, 60*a* of the aerosol delivery device 1, 51 are described for use with a solution. It should be understood that this solution may comprise certain constituents or substances that may have a stimulatory effect on the user. These constituents or substances may be of any kind that is suitable for being delivered via inhalation. The solution in which the constituents or substances are held or dissolved may primarily consist of water, ethanol, glycerol, propylene glycol or mixtures of the aforementioned solvents. By means of a sufficiently high degree of dilution in an easily volatile solvent, such as ethanol and/or water, even substances which are otherwise difficult to evaporate can evaporate in a substantially residue-free manner, and thermal decomposition of the liquid material can be avoided or significantly reduced.

It should be understood that the term "channel" used herein is not limited to a specific cross-section. Furthermore, the channel may be completely enclosed about the longitudinal axis of the channel, however it should also be appreciated that the channel may not be enclosed but open along a section parallel to the longitudinal axis of the channel.

It is also envisaged that the aerosol-forming member 10*a*, 60*a* according to any of the embodiments described above may be oxidized or coated with a non-conductive material so as to prevent a short circuit.

In order to address various issues and advance the art, the entirety of this disclosure shows by way of illustration various embodiments in which that which is claimed may be practiced and provide for a superior aerosol-forming member, aerosol delivery device component and aerosol delivery device. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

The invention claimed is:

1. An aerosol-forming member comprising:
   a sheet of material configured to wick and to heat a solution, the sheet of material having a first section and a second section, the first section extending at an angle relative to the second section, wherein the first section is configured to be heated relative to the second section, and wherein the second section extends about the first section so as to form a channel in which the first section is suspended.

2. An aerosol-forming member according to claim 1, wherein the sheet of material further comprises a third section extending from the first section.

3. An aerosol-forming member according to claim 2, wherein the first section is configured to be heated relative to the third section.

4. An aerosol-forming member according to claim 2, wherein the second and third sections extend about the first section so as to form a channel in which the first section is suspended.

5. An aerosol-forming member according to claim 2, wherein the first section extends between the second and third sections, and the second and third sections extend at an angle relative to the first section so as to form a channel.

6. An aerosol-forming member according to claim 1, wherein the first section is planar.

7. An aerosol-forming member according to claim 1, wherein the sheet of material comprises a capillary structure configured to wick a solution.

8. An aerosol-forming member according to claim 7, wherein the capillary structure is exposed on both sides of the sheet of material.

9. An aerosol-forming member according to claim 1, wherein the sheet of material comprises a first layer capable of being heated and a second layer comprising a capillary structure.

10. An aerosol-forming member according to claim 1, wherein the sheet of material is formed with slots extending across at least one of the second or third sections towards the first section so as to enable the first section to be heated relative to the at least one of the second or third sections.

11. An aerosol-forming member according to claim 2, wherein at least two of the first, second and third sections are discrete portions joined together, and the first section is made of a material that is capable of being heated relative to the material of at least one of the second or third sections.

12. An aerosol-forming member according to claim 1, wherein the sheet of material is formed from a first set of fibers, and a second set of fibers is incorporated into the first section, wherein the second set of fibers is capable of being heated relative to the first set of fibers.

13. An aerosol delivery device component comprising:
an air inlet and an air outlet fluidly communicating via an aerosol chamber defined by a chamber wall; and
an aerosol-forming member according to claim 1, wherein the aerosol-forming member is at least partially located in the aerosol chamber.

14. An aerosol delivery device component according to claim 13, wherein the sheet of material comprises two opposing major surfaces that are aligned with a direction of flow of air through the aerosol chamber.

15. An aerosol delivery device component according to claim 13, wherein at least a portion of the second section contacts the chamber wall and the first section is suspended across the aerosol chamber.

16. An aerosol delivery device component according to claim 13, wherein a shape of the aerosol chamber corresponds to a shape of the aerosol-forming member such that the aerosol-forming member contacts the chamber wall.

17. An aerosol delivery device component according to claim 13, wherein the chamber wall comprises a liquid reservoir matrix configured to replenish the aerosol-forming member with a solution.

18. An aerosol delivery device component according to claim 17, wherein the liquid reservoir matrix has a capillary structure.

19. An aerosol delivery device component according to claim 18, wherein at least the second section contacts the liquid reservoir matrix, and a capillary structure of the aerosol-forming member and the capillary structure of the liquid reservoir matrix fluidly communicate with each other.

20. An aerosol delivery device component according to claim 13, further comprising a heat shield located in the aerosol chamber against the chamber wall.

21. An aerosol delivery device comprising an aerosol delivery device component as claimed in claim 13.

22. An aerosol delivery device comprising an aerosol-forming member as claimed in claim 1.

* * * * *